(12) United States Patent
Donnelly et al.

(10) Patent No.: US 7,286,628 B2
(45) Date of Patent: Oct. 23, 2007

(54) PHASE-CONTRAST ENHANCED COMPUTED TOMOGRAPHY

(75) Inventors: Edwin F. Donnelly, Brentwood, TN (US); Ronald R. Price, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 94 days.

(21) Appl. No.: 10/494,635

(22) PCT Filed: Oct. 30, 2002

(86) PCT No.: PCT/US02/34605

§ 371 (c)(1),
(2), (4) Date: Mar. 4, 2005

(87) PCT Pub. No.: WO03/040712

PCT Pub. Date: May 15, 2003

(65) Prior Publication Data

US 2005/0129169 A1    Jun. 16, 2005

Related U.S. Application Data

(60) Provisional application No. 60/338,942, filed on Nov. 5, 2001.

(51) Int. Cl.
*A61B 6/00* (2006.01)
(52) U.S. Cl. .............................. 378/4; 378/70; 378/84
(58) Field of Classification Search ............ 378/4, 378/70, 71, 79, 84, 85, 20, 21, 62, 86, 87
See application file for complete search history.

(56) References Cited

U.S. PATENT DOCUMENTS

| | | | |
|---|---|---|---|
| 4,002,906 A | 1/1977 | Pekau et al. ............ 250/315 R |
| 4,029,960 A | 6/1977 | Pekau et al. ............ 250/315 A |
| 5,012,498 A | 4/1991 | Cuzin et al. ................ 378/22 |
| 5,173,928 A | 12/1992 | Momose et al. ............... 378/4 |
| 5,259,013 A | 11/1993 | Kuriyama et al. ........... 378/43 |
| 5,434,901 A | 7/1995 | Nagai et al. ................ 378/43 |
| 5,550,887 A | 8/1996 | Schmal et al. .............. 378/43 |
| 5,715,291 A | 2/1998 | Momose ...................... 378/84 |
| 5,802,137 A | 9/1998 | Wilkins ....................... 378/85 |
| 5,812,629 A | 9/1998 | Clauser ....................... 378/62 |
| 5,850,425 A | 12/1998 | Wilkins ....................... 378/85 |
| 5,881,126 A | 3/1999 | Momose ...................... 378/36 |
| 5,912,939 A | 6/1999 | Hirsch ......................... 378/43 |
| 5,930,325 A | 7/1999 | Momose ...................... 378/36 |
| 6,018,564 A | 1/2000 | Wilkins ....................... 378/62 |
| 6,118,850 A | 9/2000 | Mayo et al. ................. 378/83 |
| 6,163,590 A | 12/2000 | Wilkins ....................... 378/43 |
| 6,212,254 B1 | 4/2001 | Wilkins ....................... 378/62 |

FOREIGN PATENT DOCUMENTS

JP    10-248833    9/1998

OTHER PUBLICATIONS

Bonse, "Developments in x-ray tomography II," *Tech. Conf.*, SPIE vol. 3772, 1999.

(Continued)

*Primary Examiner*—Courtney Thomas
(74) *Attorney, Agent, or Firm*—Fulbright & Jaworski L.L.P.

(57) ABSTRACT

A phase-contrast x-ray computed tomography scanner, a monochromatic diffraction computed tomography scanner, a rotatable monochromatic diffraction computed tomography scanner, and a combination phase-contrast and monochromatic computed tomography scanner are provided. In addition, a method of identifying an unknown sample is provided.

29 Claims, 3 Drawing Sheets

Phase-Contrast CT Scanner

OTHER PUBLICATIONS

Fitzgerald, "Phase sensitive X-ray imaging: new approaches that can detect x-ray phase shifts within soft tissues promise for clinical and biological applications," *Physics Today Online*, vol. 53:7, http://www.aip.org/pt/vol-53/iss-7/current, 2000.

Kotre and Birch, "Phase contrast enhancement of x-ray mammography: a design study," *Phys. Med. Biol.*, 44:2853-2866, 1999.

Lagomarsino et al., "Phase contrast hard-x-ray microscopy with submicron resolution," *Appl. Phys. Lett.*, 71(18)2557-2558, 1997.

Nugent, Gureyev, Cookson, Paganin, Barnes, "Quantitative phase imaging using hard x-rays," *Phy. Rev. Lett.*, 77(14):2961-2964, 1996.

Van Dyck, Sassov, Claes, Ceulemans, "Phase-contrast x-ray microtomography," *NDTnet*, 3:8, 1998.

Rotatable Monochromatic Diffraction CT Scanner

PHASE-CONTRAST ENHANCED COMPUTED TOMOGRAPHY

This application is a national phase application under 35 U.S.C. § 371 of International Application No. PCT/US02/34605 filed Oct. 30, 2002, which claims priority to U.S. application Ser. No. 10/278,055 filed Oct. 22, 2002 and U.S. Provisional Application Ser. No. 60/338,942 filed Nov. 5, 2001. The above listed applications are incorporated into this application by reference.

BACKGROUND OF THE INVENTION

1. Field of the Invention

The present invention relates generally to the fields of radiography and tomography. More particularly, this disclosure describes how a standard x-ray source may be used to create phase-enhanced computed tomography (CT) images. These phase-enhanced CT images provide sharper images which make small edges, including small masses or small spiculations, more evident. This provides a method for, among other things, the inspection of organic materials and for use in medical apparatuses.

2. Description of Related Art

In the conventional x-ray transmission imaging system, the contrast of an obtained image depends upon the degree of absorption of x-rays by an object. Namely, if there is a region where heavy elements with high x-ray absorptance are dense, that portion exhibits a low transmittance and can be caught as a shadow in an image. On the other hand, objects made of light elements (soft tissues, etc.) are transparent to x-rays and are therefore difficult to obtain an image contrast. For example, in many clinical situations, such as mammography, there is a need to distinguish between different kinds of soft tissue, between tumors and normal tissue, for instance. Accordingly, there is employed a method in which the contrast is emphasized by injecting heavy elements as a contrast agent in order to observe biological soft tissues (such as internal organs, tumors, or blood vessels), for example, when an x-ray cross section image for medical diagnosis is to be acquired. However, the contrasting technique cannot always be applied to all observation locations to be investigated. Also, the contrasting process may negatively impact the body.

The above problem concerning the image contrast exists similarly even in x-ray computerized tomography (CT) which is a three-dimensional, inside-observing technique. A CT scanner x-rays the body from many angles. The x-ray beams are detected by the CT scanner and analyzed by a computer. The computer compiles the images into a picture of the body area being scanned. These images can then be viewed on a monitor or reproduced as photographs.

In lieu of x-ray absorption techniques, there is an imaging method available for obtaining a contrast by monitoring x-ray phase shifts. A phase-contrast x-ray records information from the x-ray beams after they have passed through different materials, including biological soft tissues. All tissues cause the x-rays to slow down, resulting in what is known as a phase shift. The size of the shift depends on the type of tissue. Phase-sensitive techniques, which can be understood using wave optics rather than ray optics, offer ways to augment or complement standard absorption contrast by incorporating phase information. Also, since phase-contrast relies only on refraction of x-rays, not on absorption, imaging can be done at higher energies where the absorbed radiation dose can be less, thereby reducing potential damage to tissues.

The use of phase-contrast imaging methods enables observation with an excellent sensitivity which is one-thousand times as high as that in the conventional absorption-contrast method. Thus it may be possible to observe phase contrast when absorption contrast is undetectable. Furthermore, biological soft tissues can be observed without being subjected to a specific contrasting process. Also, even if a contrast agent is used, the choice of a wider variety of contrast agents and contrasting techniques are possible.

There has been devised a phase-contrast x-ray CT apparatus in which phase contrast is introduced to the x-ray CT enabling three-dimensional observation. U.S. Pat. No. 5,173,928 is specifically incorporated herein by reference in its entirety. According to the disclosed technique of the '928 patent, an x-ray interferometer is used to reconstruct an image in a virtual-cross section from interference patterns. This disclosed technique is limited to observing an object having a diameter of only several millimeters, and therefore is not practical for medical diagnosis. Further problems with the above system using the x-ray interferometer is that (1) in order to ensure coherency, the energy band of an x-ray beam must be narrowed to obtain a high monochromaticity and hence a bright light source such as synchrotron radiation must be used; and (2) that a precision optical system is required and it is therefore difficult to handle the system.

There has also been devised a phase contrast x-ray CT apparatus in which an x-ray interferometer is not used. U.S. Pat. No. 5,715,291 is specifically incorporated herein by reference in its entirety. In the '291 patent, the phase distribution is determined from the distribution of refraction angles of x-rays transmitted through an object. However, this disclosure is limited to object rotation to acquire the necessary data to reconstruct a CT image.

In view of the shortcomings such as those listed above, improved phase-contrast imaging techniques would be desirable.

SUMMARY OF THE INVENTION

The present invention discloses methods and apparatuses that are capable of obtaining accurate and well-defined x-ray images of samples such as soft tissues in humans. This invention is envisioned for use in medical diagnosis purposes but in no way is so-limited. In fact, it may be used to study any type of sample.

Breast cancer screening is such an example of the applicability of Applicants invention. Current mammography screening has a very high rate of false positives and false negatives (Fitzgerald, 2001). In a population of undiagnosed women advised by their doctors to have regular diagnostic screening, only five women out of 1000 will actually have breast cancer (Fitzgerald, 2001). But for that same population, the rate of positive mammograms will be 10% (Fitzgerald, 2001). The ratio of false positives to true positives is nearly 20:1 and for about 10–20% of women who have palpable abnormalities, the mammograms won't show anything (Fitzgerald, 2001). Mammography screening is such an example of the driving need to improve the current phase contrast x-ray CT apparatuses to obtain more accurate and sharper x-ray images of soft tissue.

The present invention is applicable but not limited to methods of computed tomography images of sample objects and to medical inspection apparatuses which employ phase shift technology to obtain computed tomography images.

One embodiment of the present disclosure is to provide an apparatus which creates phase-contrasted CT images based on interference effects which take advantage of geometry so that both lateral coherence and demonstration of phase effects result from the manner in which the source and detector are placed relative to the object. Specifically, the invention provides for a phase-contrast computed tomography scanner which allows the user to obtain phase-contrast, x-ray computed tomography images of a sample object. The samples that can be scanned by this CT scanner are unlimited. However, in one embodiment, the sample includes biological soft tissues. A suitable CT scanner may use a polychromatic x-ray source. There may also be a power supply source coupled to the polychromatic x-ray source to power it, and a first translation stage may be coupled to the power supply source. A rotational stage may be in spaced relation with the translation stage and configured to hold and rotate the sample. The polychromatic x-ray source may be spaced sufficiently far from the rotational stage so that x-rays reaching the rotational stage are substantially coherent. There is a detector in spaced relation with the rotational stage and configured to collect phase contrast x-ray data from the sample. There may also be second translation stage coupled to the detector and a computer coupled to the detector and configured to form a computed tomography image of the sample using the phase-contrast x-ray data The CT scanner may even provide that the computer controls the power supply source, the first translation stage, the rotational stage, and the second translation stage. In another aspect of this embodiment of the present disclosure, an existing x-ray source may be interchanged with a polychromatic x-ray source, which would enable the existing x-ray source to perform phase-contrast imaging. In yet another aspect of this embodiment of the present disclosure, a suitable polychromatic x-ray source may include an x-ray tube, a radioactive source and/or a synchrotron radiation source. Finally, the CT scanner may even further provide that the polychromatic x-ray source operates between a 20 and 150 kilovoltage potential kVp) and wherein the polychromatic x-ray source is spaced about four meters from the rotational stage.

In another embodiment of this disclosure, there is provided an apparatus which creates phase-contrasted CT images based on interference effects in which both coherence and imaging require the use of perfect crystals. As used herein, a "perfect crystal" is one in which there are no substantial point, linear, or planar imperfections. Specifically, this embodiment of the present invention provides a monochromatic diffraction computed tomography scanner which allows the user to obtain phase-contrast, x-ray computed tomography images of a sample object. The samples that can be scanned by this CT scanner are unlimited. However, in one embodiment, the sample includes biological soft tissues. This CT scanner may include a polychromatic x-ray source. There is also a power supply source coupled to the polychromatic x-ray source to power the polychromatic x-ray source. There is a first translation stage coupled to the power supply source. There is also a pair of rotatable, interchangeable monochromator crystals in spaced relation with the polychromatic x-ray source. A rotational stage in spaced relation with the monochromator crystals and configured to hold and rotate the sample is also included. There is a rotatable, interchangeable analyzer crystal in spaced relation with the rotational stage. There is also a detector in spaced relation with the analyzer crystal and configured to collect phase contrast x-ray data from the sample. A second translation stage coupled to the detector and a computer coupled to the detector and configured to form a computed tomography image of the sample using the phase-contrast x-ray data also exists. This CT scanner may even provide that the computer controls the power supply source, the pair of rotatable interchangeable monochromator crystals, the first translation stage, the rotational stage, the rotatable interchangeable analyzer crystal and/or the second translation stage. In another aspect of this embodiment of this disclosure, the polychromatic x-ray source may include an x-ray tube, a radioactive source and/or a synchrotron radiation source. The CT scanner may even further provide that the polychromatic x-ray source operates at a range between 20 and 150 kVp. This CT scanner may further provide that the pair of monochromator crystals and the analyzer crystal may be selected from a group of non-perfect crystals. However, in one embodiment, the pair of monochromator crystals and the analyzer crystal may be perfect silicon crystals. Finally, in yet another aspect of, this present disclosure, an existing x-ray source can be interchanged with the polychromatic x-ray source which would enable the existing x-ray source to perform phase-contrast imaging.

In yet another embodiment of the present invention, a rotatable monochromatic diffraction computed scanner is disclosed which employs object rotation, polychromatic x-ray source rotation and detector rotation to obtain phase contrast images. The samples that can be scanned by this CT scanner are unlimited. However, in one embodiment, the sample may include biological soft tissues. This CT scanner may include a polychromatic x-ray source configured to rotate about the sample. There may also be a power supply source coupled to the polychromatic x-ray source to power it. There may be a pair of interchangeable monochromator crystals that may be in spaced relation with the polychromatic x-ray source and configured to rotate with the polychromatic x-ray source about the sample. There may be a fixed stage that may be in spaced relation with the monochromator crystals and configured to hold the sample in a fixed position. There may also be a interchangeable analyzer crystal that may be in spaced relation with the fixed stage and configured to rotate with the polychromatic x-ray source about the sample. A detector may be in spaced relation with the analyzer crystal and configured to rotate with the polychromatic x-ray source about the sample to collect phase-contrast x-ray data from the sample. There may be a translation stage coupled to the power supply source, the pair of interchangeable monochromator crystals, the interchangeable analyzer crystal and the detector. There may also be a computer coupled to the detector and configured to form a computed tomography image of the sample using the phase-contrast x-ray data. The CT scanner may even provide that the computer controls the power supply source and the translation stage. In another aspect of this embodiment of the present disclosure, the polychromatic x-ray source may include an x-ray tube, a radioactive source and/or a synchrotron radiation source. In yet another aspect of this embodiment, the CT scanner may even further provide that the polychromatic x-ray source may operate at a range between 20 and 150 kVp. Finally, this CT scanner may further provide that the pair of monochromator crystals and the analyzer crystal may be selected from a group of non-perfect crystals. In one embodiment, the pair of monochromator crystals and the analyzer crystal may be perfect silicon crystals.

In still another embodiment of the present disclosure, the relevant technology of the phase-contrast computed tomography scanner and the monochromatic diffraction computed tomography scanner are combined together to form a CT scanner which may be used to create phase-contrast CT images. Specifically, the present disclosure provides a combination phase contrast and monochromatic diffraction computed tomography scanner which allows the user to obtain phase-contrast, x-ray computed tomography images of a sample object. The samples that can be scanned by this CT scanner are unlimited. However, in one embodiment, the sample may include biological soft tissues. This CT scanner may include a polychromatic x-ray source. There may also be a first translation stage coupled to the power supply source. There may be a power supply source coupled to the polychromatic x-ray source to power the polychromatic x-ray source. There may also be a pair of rotatable, interchangeable monochromator crystals in spaced relation with the polychromatic x-ray source and configured to occupy at least two positions, one position being aligned with the polychromatic x-ray source and the other position being out of alignment with the polychromatic x-ray source. A rotational stage in spaced relation with the monochromator crystals and configured to hold the sample may also included. There may also be a rotatable, interchangeable analyzer crystal in spaced relation with the rotational stage and configured to occupy at least two positions, one position being aligned with the sample and the other position being out of alignment with the sample. There may be a detector in spaced relation with the rotational stage and configured to collect phase-contrast x-ray data from the sample. There may also be a computer coupled to the detector and configured to form a computed tomography image of the sample using the phase-contrast x-ray data. This CT scanner may even further provide that the computer controls the power supply source, the pair of rotatable interchangeable monochromator crystals, the first translation stage, the rotational stage, the rotatable interchangeable analyzer crystal and/or the second translation stage. In another aspect of this embodiment of the present disclosure, the polychromatic x-ray source may include an x-ray tube, a radioactive source and/or a synchrotron radiation source In yet another aspect of this embodiment, the polychromatic x-ray source may operate at a range between 20 and 150 kVp. The CT scanner may even further provide that the pair of monochromator crystals and the analyzer crystal may be selected from a group of non-perfect crystals. In one embodiment, the pair of monochromator crystals and the analyzer crystal may be perfect silicon crystals. Finally, in another aspect of this disclosure, an existing x-ray source can be interchanged with the polychromatic x-ray source which would enable the existing x-ray source to perform phase-contrast imaging.

In yet another embodiment of the present disclosure, there is provided a method of identifying an unknown sample. This method my include obtaining a known sample and then obtaining a phase-contrast, x-ray computed tomography image of the known sample and identify a diffraction pattern for the known sample using the x-ray computed tomography image of the known sample. Then, associate the diffraction pattern of the known sample with the known sample in a database. Then, one can obtain a phase-contrast, x-ray computed tomography image of an unknown sample and identify a diffraction pattern for the unknown sample using the x-ray computed tomography image of the unknown sample and correlate the diffraction pattern of the unknown sample with the diffraction pattern of a known sample using the database to identify the unknown sample. The samples that can be scanned by this CT scanner are unlimited. However, in one embodiment, the sample may include biological soft tissues.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. These drawings illustrate by way of example and not limitation, and they use like references to indicate similar elements. The drawings include.

DESCRIPTION OF ILLUSTRATIVE EMBODIMENTS

Figure 1:
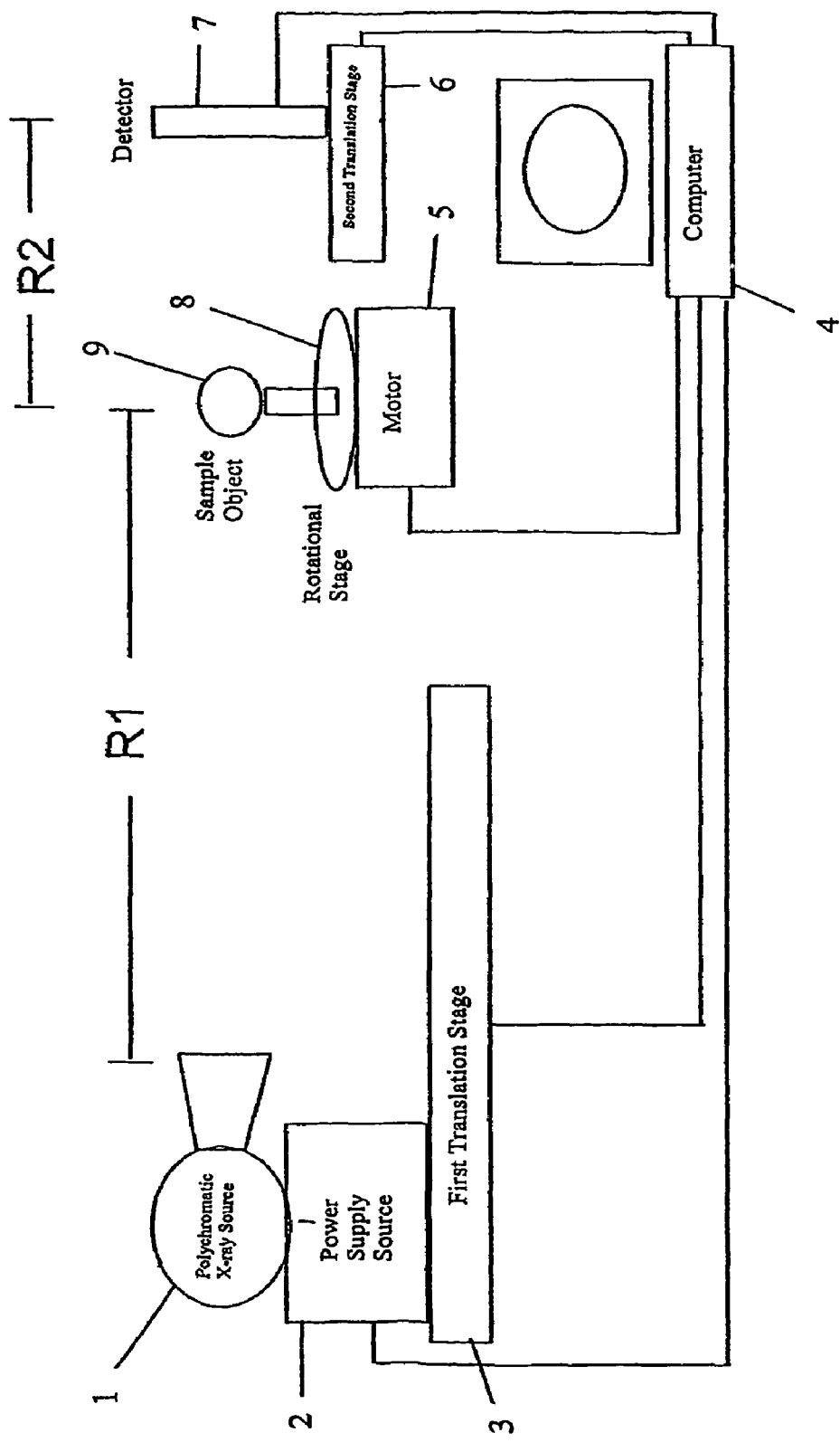
FIG. 1—is a drawing of a phase-contrast computed tomography scanner according to an embodiment of the present disclosure.

FIG. 1 illustrates one possible construction of a phase-contrast computed tomography scanner for providing phase-contrast, x-ray computed tomography images of a sample. A polychromatic x-ray source 1 may be connected to and powered by a power supply source 2. In one embodiment, the polychromatic x-ray source 1 may be selected from a group including an x-ray tube, a radioactive source and/or a synchrotron radiation source. The power supply source 2 may operate between a range of 20 and 150 kilovoltage potential. The power supply source 2 may be connected to a computer 4. The computer 4 may control the kilovoltage output of the power supply source 2. In another embodiment, the power supply source 2 may be controlled independent of the computer 4. The polychromatic x-ray source 1 may be situated on top of the power supply source 2. The power supply source 2 may be situated on top of a first translation stage 3. The first translation stage 3 can be maneuvered through an x-axis, a y-axis and/or z-axis by mechanical knobs. However, in one embodiment, the computer 4 may operate and maneuver the first translation stage 3 through the x-axis, y-axis and/or z-axis. The polychromatic x-ray source 1 may be about 4 meters away from a rotational stage 8 as exemplified by R1 in FIG. 1. The rotational stage 8 may be capable of supporting a sample object 9 for the purposes of scanning the sample object 9 with the polychromatic x-ray source 1. The rotational stage 8 may be situated on top of a motor 5 in which the motor 5 may be capable of rotating the rotational stage 8 360 degrees. The sample object 9 may be placed a suitable distance R2 from the detector 7 to ensure that the detector 7 may be able to collect phase-contrast x-ray data from the sample 9. Those of ordinary skill will recognize that R2 may thus vary widely. The detector 7 may be capable of detecting x-ray beams after they have passed through the sample object 9. The detector 7 may be situated on top of a second translation stage 6. The second translation stage 6 can be maneuvered through an x-axis, a y-axis and/or z-axis by mechanical knobs. However, in one embodiment, the computer 4 can operate and maneuver the second translation stage 6 through the x-axis, y-axis and/or z-axis. The computer 4 may be capable of analyzing the phase shift of the x-ray beams that have passed through the sample object 9, thus creating a CT image of the sample object 9 on the computer's 4 monitor. The computer 4 may also be capable of operating the power supply source 2, the first translation stage 3, the motor 5 that is capable of rotating the rotational stage 8 360 degrees, the second translation stage 6, and/or the detector 7.

Figure 2:
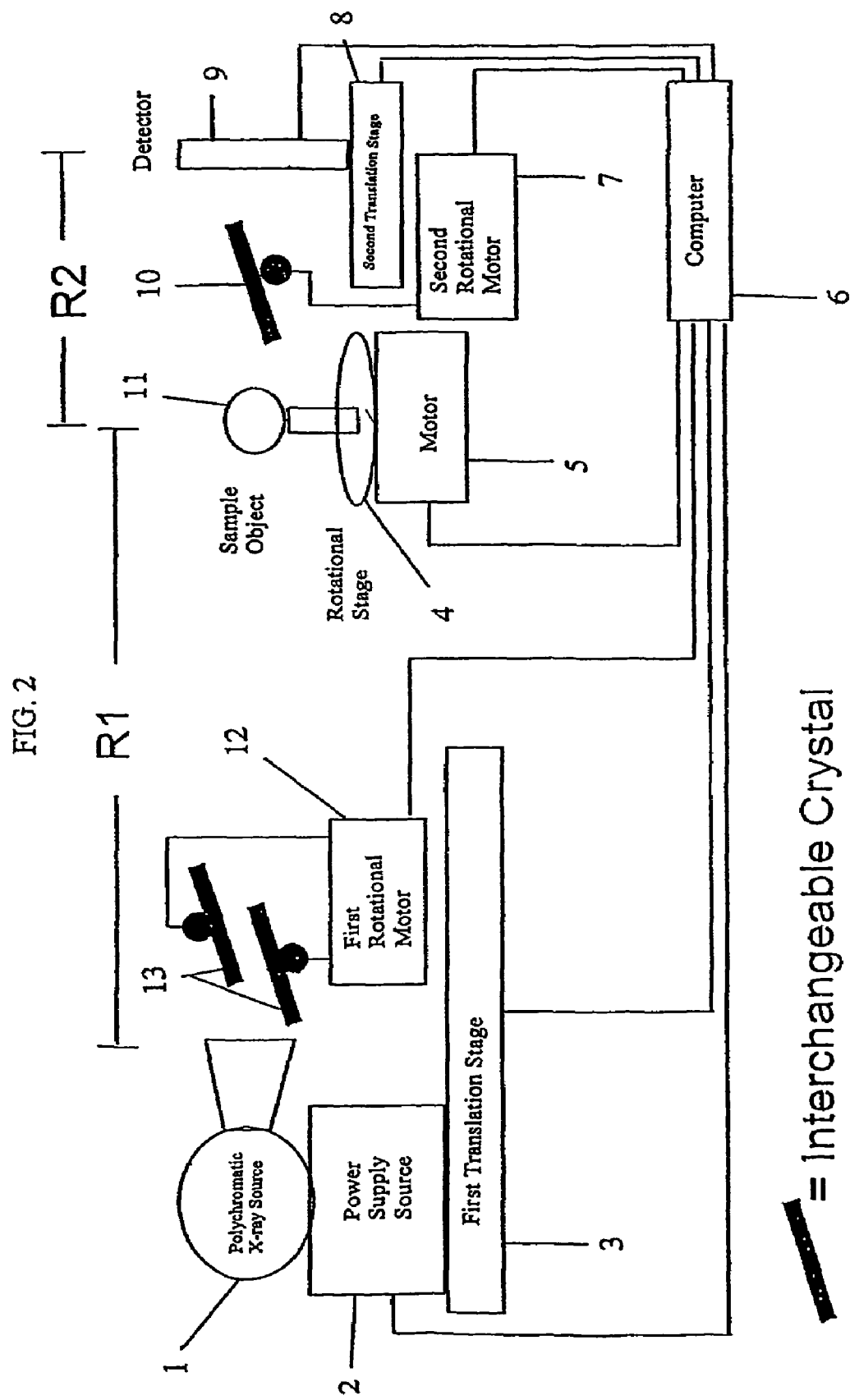
FIG. 2—is a drawing of a monochromatic diffraction computed tomography scanner and a combination phase-contrast and monochromatic diffraction computed tomography scanner according to an embodiment of the present disclosure.

FIG. 2 illustrates a possible construction of a monochromatic diffraction computed tomography scanner for providing phase-contrast, x-ray computed tomography images of a sample. A polychromatic x-ray source 1 may be connected to and powered by a power supply source 2. In one embodiment, the polychromatic x-ray source 1 is selected from a group including an x-ray tube, a radioactive source and/or a synchrotron radiation source. The power supply source 2 may operate between a 20 and 150 kilovoltage potential. The power supply source 2 may be connected to a computer 6. The computer 6 can control the kilovoltage output of the power supply source 2. In another embodiment, the power supply source 2 can be controlled independent of the computer 6. The polychromatic x-ray source 1 may be situated on top of the power supply source 2. The power supply source 2 may be situated on top of a first translation stage 3. The first translation stage 3 can be maneuvered through an x-axis, a y-axis and/or z-axis by mechanical knobs. However, in one embodiment, the computer 6 can operate and maneuver the first translation stage 3 through the x-axis, y-axis and/or z-axis. A pair of interchangeable monochromator crystals 13 may be affixed to a first rotational motor 12 In one embodiment, the pair of interchangeable monochromator crystals 13 may be perfect silicon crystals. In another embodiment, the pair of monochromator crystals may be selected from a group of non-perfect crystals. The pair of interchangeable monochromator crystals 13 may be placed a suitable distance from the polychromatic x-ray source 1 to ensure that the x-rays emerging from the monochromator crystals 13 are essentially parallel. Those of ordinary skill will recognize that this distance may thus vary widely. A first rotational motor 12 may be capable of rotating the pair of interchangeable monochromator crystals 13 360 degrees. The x-ray 1 source may be a suitable distance R1 from a sample object 11 to ensure that the x-ray beams traverse the sample object 11. Those of ordinary skill will recognize that this distance may thus vary widely. The rotational stage 4 may be capable of supporting the sample object 11 to be scanned. The rotational stage may be affixed to a motor 5. The motor 5 may be capable of rotating the rotational stage 4 360 degrees. A rotatable interchangeable analyzer crystal 10 may be placed in front of the sample object 11 to be scanned. In one embodiment, the rotatable interchangeable analyzer crystal 10 is a perfect silicon crystal. In another embodiment, the rotatable interchangeable analyzer crystal 10 may be selected from a group of non-perfect crystals. The rotatable interchangeable analyzer crystal 10 may be a suitable distance from the sample object 11 to ensure that the x-ray beams emerging from the sample object 11 are directed to the analyzer crystal 10. Those of ordinary skill will recognize that this distance may thus vary widely. The rotatable interchangeable analyzer crystal 10 may be affixed to a second rotational motor 7. The second rotational motor 7 may be capable of rotating the rotatable interchangeable analyzer crystal 10 360 degrees. The sample object 11 may be placed a suitable distance R2 from the detector 9 to ensure that the detector 9 may be able to collect phase-contrast x-ray data from the sample. Those of ordinary skill will recognize that R2 may thus vary widely. The detector 9 may be configured to collect phase-contrast x-ray data from the x-ray beams passing through the sample object 11. The detector 9 may be situated on top of a second translation stage 8. The second translation stage 8 can be maneuvered through an x-axis, a y-axis and/or z-axis by mechanical knobs. However, in one embodiment, the computer 6 may operate and maneuver the second translation stage 8 through the x-axis, y-axis and/or z-axis. The computer 6 may be capable of analyzing the phase shift of the x-ray beams that have passed through the sample object 11, thus creating a CT image of the sample object 11 on the computer's 6 monitor. The computer 6 may also be capable of operating the power supply source 2, the first translation stage 3, the first rotational motor 12, the motor 5 that is affixed to the rotational stage 4, the second rotational motor 7, the second translation stage 8 and/or the detector 9. In another embodiment of this invention, an existing x-ray source may be interchanged with the polychromatic x-ray source 1.

FIG. 2 also illustrates a possible construction of a combination phase-contrast and monochromatic diffraction computed tomography scanner for providing phase-contrast, x-ray computed tomography images of a sample. A polychromatic x-ray source 1 may be connected to and powered by a power supply source 2. In one embodiment, the polychromatic x-ray source 1 may be selected from a group including an x-ray tube, a radioactive source and/or a synchrotron radiation source. The power supply source 2 may operate between a 20 and 150 kilovoltage potential. The power supply source 2 may be connected to a computer 6. The computer 6 can control the kilovoltage output of the power supply source 2. In another embodiment, the power supply source 2 may be controlled independent of the computer 6. The polychromatic x-ray source 1 may be situated on top of the power supply source 2. The power supply source 2 may be situated on top of a first translation stage 3. The first translation stage 3 may be maneuvered through an x-axis, a y-axis and/or z-axis by mechanical knobs. However, in one embodiment, the computer 6 may operate and maneuver the first translation stage 3 through the x-axis, y-axis and/or z-axis. A pair of interchangeable monochromator crystals 13 may be affixed to a first rotational motor 12. In one embodiment, the pair of interchangeable monochromator crystals 13 may be perfect silicon crystals. In another embodiment, the pair of monochromator crystals may be selected from a group of non-perfect crystals. The pair of interchangeable monochromator crystals 13 may be placed a suitable distance from the polychromatic x-ray source 1 to ensure that the x-rays emerging from the monochromator crystals 13 are essentially parallel. Those of ordinary skill will recognize that this distance may thus vary widely. The first rotational motor 12 may be capable of rotating the pair of interchangeable monochromator crystals 13 360 degrees. In another embodiment of this invention, the first rotational motor 12 may also be capable of configuring the interchangeable monochromator crystals 13 into at least two positions, one position being aligned with the polychromatic x-ray source and the other position being out of alignment with the polychromatic x-ray source 1. The x-ray 1 source may be a suitable distance R1 from a sample object 11 to ensure that the x-ray beams traverse the sample object 11. Those of ordinary skill will recognize that this distance may thus vary widely. A rotational stage 4 may be capable of supporting the sample object 11 to be scanned. The rotational stage may be affixed to a motor 5. The motor 5 may be capable of rotating the rotational stage 4 360 degrees. A rotatable interchangeable analyzer crystal 10 may be placed in front of the sample object 11 to be scanned. In one embodiment, the rotatable interchangeable analyzer crystal 10 may be a perfect silicon crystal. In another embodiment, the rotatable interchangeable analyzer crystal 10 may be selected: from a group of non-perfect crystals.

The rotatable interchangeable analyzer crystal 10 may be a suitable distance from the sample object 11 to ensure that the x-ray beams emerging from the sample object 11 are directed to the analyzer crystal 10. Those of ordinary skill will recognize that this distance may thus vary widely. The rotatable interchangeable analyzer crystal 10 may be affixed to a second rotational motor 7. The second rotational motor 7 may be capable of rotating the rotatable interchangeable analyzer crystal 10 360 degrees. In another embodiment of this invention, the second rotational motor 7 may also be capable of configuring the rotatable interchangeable analyzer crystal 10 into at least two positions, one position being aligned with the sample object 11 and the other position being out of alignment with the sample object 11. The sample object 11 may be placed a suitable distance R2 from the detector 9 to ensure that the detector 9 may be able to collect phase-contrast x-ray data from the sample. Those of ordinary skill will recognize that R2 may thus vary widely. The detector 9 may be configured to collect phase-contrast x-ray data from the x-ray beams passing through the sample object 11. The detector 9 may be situated on top of a second translation stage 8. The second translation stage 8 may be maneuvered through an x-axis, a y-axis and/or z-axis by mechanical knobs. However, in one embodiment, the computer 6 may operate and maneuver the second translation stage 8 through the x-axis, y-axis and/or z-axis. The computer 6 may be capable of analyzing the phase shift of the x-ray beams that have passed through the sample object 11, thus creating a CT image of the sample object 11 on the computer's 6 monitor. The computer 6 may also be capable of operating the power supply source 2, the first translation stage 3, the first rotational motor 12, the motor 5 that is affixed to the rotational stage 4, the second rotational motor 7, the second translation stage 8 and/or the detector 9. In another embodiment of this disclosure, an existing x-ray source may be interchanged with the polychromatic x-ray source 1.

Figure 3:
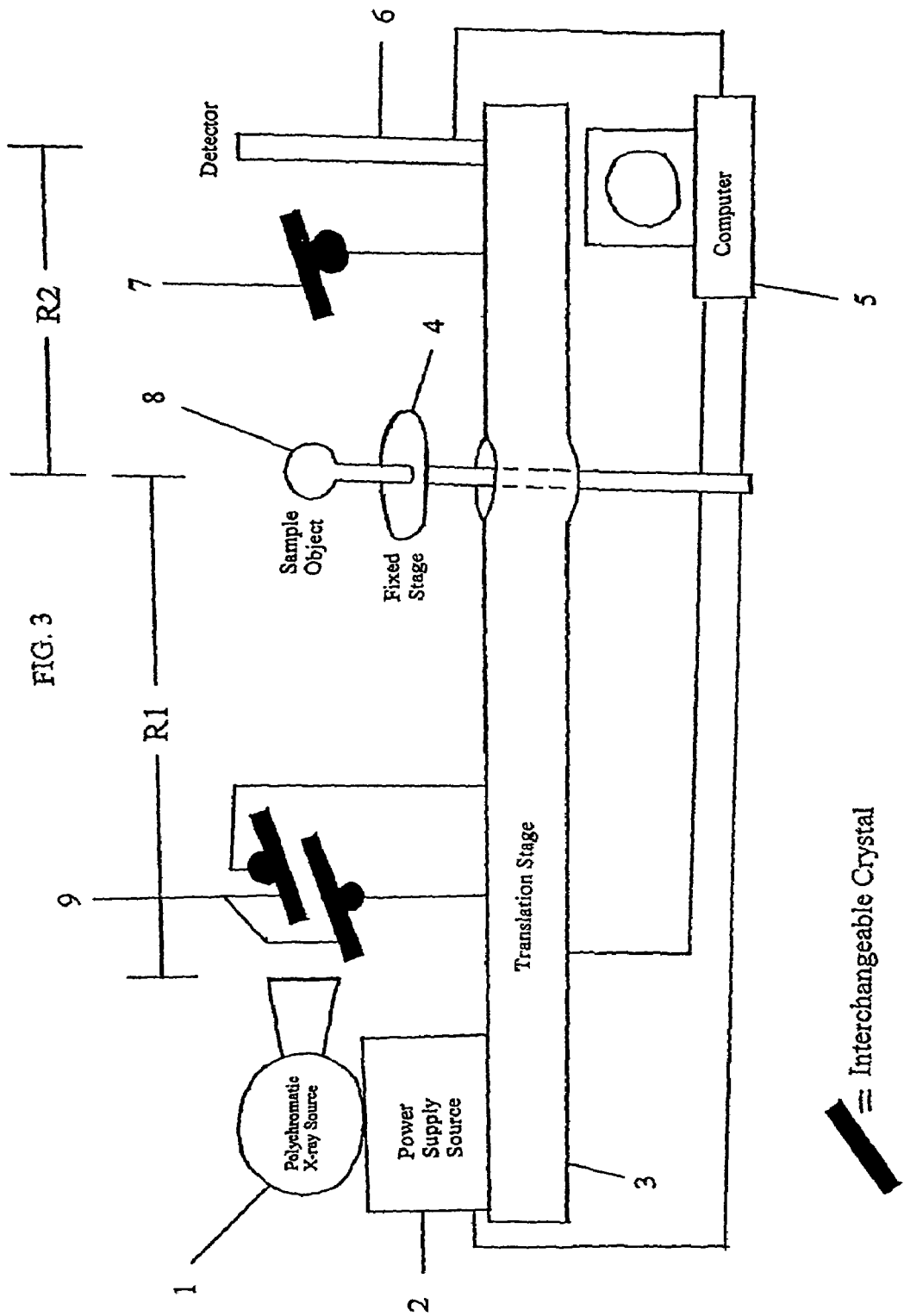
FIG. 3—is a drawing of a rotatable monochromatic diffraction computed tomography scanner according to an embodiment of the present disclosure.

FIG. 3 illustrates a possible construction of a rotatable monochromatic diffraction computed tomography scanner for providing phase-contrast, x-ray computed tomography images of a sample. A polychromatic x-ray source 1 may be connected to and powered by a power supply source 2. In one embodiment, the polychromatic x-ray source 1 may include an x-ray tube, a radioactive source and/or a synchrotron radiation source. The power supply source 2 may operate between a 20 and 150 kilovoltage potential. The power supply source 2 may be connected to a computer 5. The computer 5 may control the kilovoltage output of the power supply source 2. In another embodiment, the power supply source 2 may be controlled independent of the computer 5. The polychromatic x-ray source 1 may be situated on top of the power supply source 2. The power supply source 2 may be situated on top of a translation stage 3. The translation stage 3 can be rotated 360 degrees and/or may be maneuvered through an x-axis, a y-axis and/or z-axis by mechanical knobs. However, in one embodiment, the computer 6 may rotate the translation stage 3 360 degrees and/or maneuver the translation stage 3 through the x-axis, y-axis and/or z-axis. A pair of interchangeable monochromator crystals 9 may be affixed to the translation stage 3 and may be capable of being rotated with the polychromatic x-ray source 1 about the sample object 8. In one embodiment, the pair of interchangeable monochromator crystals 9 are perfect silicon crystals. In another embodiment, the pair of monochromator crystals may be selected from a group of non-perfect crystals. The pair of interchangeable monochromator crystals 9 may be placed a suitable distance from the polychromatic x-ray source 1 to ensure that the x-rays emerging from the monochromator crystals 9 are essentially parallel. Those of ordinary skill will recognize that this distance may thus vary widely. The x-ray 1 source may be a suitable distance R1 from a sample object 8 to ensure that the x-ray beams traverse the sample object 8. Those of ordinary skill will recognize that this distance may thus vary widely. A fixed stage 4 may be capable of supporting the sample object 8 to be scanned. The fixed stage 4 may not be affixed to the translation stage 3. A interchangeable analyzer crystal 7 can be placed in spaced relation with the sample object 8 to be scanned. In one embodiment, the interchangeable analyzer crystal 7 may be a perfect, silicon crystal. In another embodiment, the rotatable interchangeable analyzer crystal 7 may be selected from a group of non-perfect crystals. The rotatable interchangeable analyzer crystal 7 may be a suitable distance from the sample object 8 to ensure that the x-ray beams emerging from the sample object 8 are directed to the analyzer crystal 7. Those of ordinary skill will recognize that this distance may thus vary widely. The interchangeable analyzer crystal 7 may be situated on top of the translation stage 3 allowing the interchangeable analyzer crystal 7, the polychromatic x-ray source 1 and/or the pair of interchangeable monochromator crystals 9 to rotate about the sample object 8. The sample object 8 may be placed a suitable distance R2 from the detector 6 to ensure that the detector 6 may be able to collect phase-contrast x-ray data from the sample object 8. Those of ordinary skill will recognize that R2 may thus vary widely. The detector 6 may be configured to collect phase-contrast x-ray data from the x-ray beams passing through the sample object 8. The detector 6 may be situated on top of the translation stage 3 allowing the detector 6, the polychromatic x-ray source 1, the pair of interchangeable monochromator crystals 9 and/or the interchangeable analyzer crystal 7 to rotate about the sample. The computer S may be capable of analyzing the phase shift of the x-ray beams that have passed through the sample object 8, thus creating a CT image of the sample object 8 on the computer's 5 monitor. The computer 5 may also be capable of operating the power supply source 2, the translation stage 3 and/or the detector 6.

All of the apparatuses and methods disclosed and claimed herein can be made and executed without undue experimentation in light of the present disclosure. While the apparatuses and methods of this invention have been described in terms of preferred embodiments, it will be apparent to those of skill in the art that variations may be applied to the apparatuses and methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,802,137
U.S. Pat. No. 5,550,887
U.S. Pat. No. 5,259,013
U.S. Pat. No. 5,850,425
U.S. Pat. No. 6,212,254
U.S. Pat. No. 5,715,291

U.S. Pat. No. 6,163,590
U.S. Pat. No. 6,018,564
U.S. Pat. No. 5,930,325
U.S. Pat. No. 5,912,939
U.S. Pat. No. 5,881,126
U.S. Pat. No. 5,434,901
U.S. Pat. No. 5,173,928
U.S. Pat. No. 4,029,960
U.S. Pat. No. 4,002,906
Japanese Application No. 10-248833
Van Dyck, Sassov, Claes, Ceulemans, "Phase-contrast x-ray microtomography," *NDTnet,* 3:8, 1998.
Kotre and Birch, "Phase contrast enhancement of x-ray mammography: a design study," *Phys. Med. Biol.,* 44:2853–2866, 1999.
Ingal and Beliaevskaya, "Phase radiography—a new technique of x-ray imaging," www.xraysite.com/knowbase/phaseradiology.
Bonse, "Developments in x-ray tomography II," Tech. Conf., SPIE Vol. 3772, 1999.
Lagomarsino et al., "Phase contrast hard-x-ray microscopy with submicron resolution," *Appl. Phys. Lett.,* 71(18) 2557–2558, 1997.
Fitzgerald, Physics Today Online, Vol. 53:7, http://www.aip.org/pt/vol-53/iss-7/current, 2000.
Nugent, Gureyev, Cookson, Paganin, Barnes, "Quantitative phase imaging using hard x-rays," *Phy. Rev. Lett.,* 77(14): 2961–2964, 1996.

The invention claimed is:

1. A phase-contrast computed tomography scanner for providing phase-contrast, x-ray computed tomography images of a sample, comprising:
a polychromatic x-ray source;
a power supply source coupled to the polychromatic x-ray source to power the polychromatic x-ray source;
a first translation stage coupled to the power supply source;
a rotational stage in spaced relation with the translation stage and configured to hold and rotate the sample;
wherein the polychromatic x-ray source is spaced from the rotational stage so that x-rays reaching the rotational stage are substantially coherent;
a detector in spaced relation with the rotational stage and configured to collect phase-contrast x-ray data from the sample;
a second translation stage coupled to the detector; and
a computer coupled to the detector and configured to form a computed tomography image of the sample using the phase-contrast x-ray data.

2. The scanner of claim 1, wherein the computer controls the power supply source, the first translation stage, the rotational stage and/or the second translation stage.

3. The scanner of claim 1, wherein an existing x-ray source is interchanged with the polychromatic x-ray source which would enable the existing x-ray source to perform phase-contrast imaging.

4. The scanner of claim 1, wherein the polychromatic x-ray source is selected from the group comprising an x-ray tube, a radioactive source and/or a synchrotron radiation source.

5. The scanner of claim 1, wherein the polychromatic x-ray source operates between 20 and 150 kilovoltage potential and wherein the polychromatic x-ray source is spaced about four meters from the rotational stage.

6. The scanner of claim 1, wherein the polychromatic x-ray source is placed about four meters from the rotational stage.

7. A monochromatic diffraction computed tomography scanner for providing phase-contrast, x-ray computed tomography images of a sample, comprising:
a polychromatic x-ray source;
a power supply source coupled to the polychromatic x-ray source to power the polychromatic x-ray source;
a first translation stage coupled to the power supply source;
a pair of rotatable, interchangeable monochromator crystals in spaced relation with the polychromatic x-ray source;
a rotational stage in spaced relation with the monochromator crystals and configured to hold and rotate the sample;
a rotatable, interchangeable analyzer crystal in spaced relation with the rotational stage;
a detector in spaced relation with the analyzer crystal and configured to collect phase-contrast x-ray data from the sample;
a second translation stage coupled to the detector; and
a computer coupled to the detector and configured to form a computed tomography image of the sample using the phase-contrast x-ray data.

8. The scanner of claim 7, wherein the computer controls the power supply source, the pair of rotatable interchangeable monochromator crystals, the first translation stage, the rotational stage, the rotatable interchangeable analyzer crystal and/or the second translation stage.

9. The scanner of claim 7, wherein the polychromatic x-ray source is selected from the group comprising an x-ray tube, a radioactive source and/or a synchrotron radiation source.

10. The scanner of claim 7, wherein the polychromatic x-ray source operates between 20 and 150 kilovoltage potential and wherein the polychromatic x-ray source is spaced about four meters from the rotational stage.

11. The scanner of claim 7, wherein the pair of monochromator crystals and wherein the analyzer crystal are selected from a group of non-perfect crystals.

12. The scanner of claim 11, wherein the pair of monochromator crystals are perfect silicon crystals and wherein the analyzer crystal is a perfect silicon crystal.

13. The scanner of claim 7, wherein an existing x-ray source is interchanged with the polychromatic x-ray source which would enable the existing x-ray source to perform phase-contrast imaging.

14. A rotatable monochromatic diffraction computed tomography scanner for providing phase-contrast, x-ray computed tomography images of a sample, comprising:
a polychromatic x-ray source configured to rotate about the sample;
a power supply source coupled to the polychromatic x-ray source to power the polychromatic x-ray source;
a pair of interchangeable monochromator crystals in spaced relation with the polychromatic x-ray source and configured to rotate with the polychromatic x-ray source about the sample;
a fixed stage in spaced relation with the monochromator crystals and configured to hold the sample in a fixed position;
a interchangeable analyzer crystal in spaced relation with the fixed stage and configured to rotate with the polychromatic x-ray source about the sample;
a detector in spaced relation with the analyzer crystal and configured to rotate with the polychromatic x-ray source about the sample to collect phase-contrast x-ray data from the sample;

a translation stage coupled to the power supply source, the pair of interchangeable monochromator crystals, the interchangeable analyzer crystal and the detector; and a computer coupled to the detector and configured to form a computed tomography image of the sample using the phase-contrast x-ray data.

15. The scanner of claim 14, wherein the computer controls the power supply source and/or the translation stage.

16. The scanner of claim 14, wherein the polychromatic x-ray source is selected from the group comprising an x-ray tube, a radioactive source and/or a synchrotron radiation source.

17. The scanner of claim 14, wherein the polychromatic x-ray source operates between 20 and 150 kilovoltage potential and wherein the polychromatic x-ray source is spaced about four meters from the rotational stage.

18. The scanner of claim 14, wherein the pair of monochromator crystals and wherein the analyzer crystal are selected from a group of non-perfect crystals.

19. The scanner of claim 18, wherein the pair of monochromator crystals are perfect silicon crystals and wherein the analyzer crystal is a perfect silicon crystal.

20. A combination phase-contrast and monochromatic diffraction computed tomography scanner for providing phase-contrast, x-ray computed tomography images of a sample, comprising:

a polychromatic x-ray source;

a power supply source coupled to the polychromatic x-ray source to power the polychromatic x-ray source;

a first translation stage coupled to the power supply source;

a pair of rotatable, interchangeable monochromator crystals in spaced relation with the polychromatic x-ray source and configured to occupy at least two positions, one position being aligned with the polychromatic x-ray source and the other position being out of alignment with the polychromatic x-ray source;

a rotational stage in spaced relation with the monochromator crystals and configured to hold the sample;

a rotatable, interchangeable analyzer crystal in spaced relation with the rotational stage and configured to occupy at least two positions, one position being aligned with the sample and the other position being out of alignment with the sample;

a detector in spaced relation with the rotational stage and configured to collect phase-contrast x-ray data from the sample; and a computer coupled to the detector and configured to form a computed tomography image of the sample using the phase-contrast x-ray data.

21. The scanner of claim 20, wherein the computer controls the power supply source, the pair of rotatable interchangeable monochromator crystals, the first translation stage, the rotational stage, the rotatable interchangeable analyzer crystal and/or the second translation stage.

22. The scanner of claim 20, wherein the polychromatic x-ray source is selected from the group comprising an x-ray tube, a radioactive source and/or a synchrotron radiation source.

23. The scanner of claim 20, wherein the polychromatic x-ray source operates between 20 and 150 kilovoltage potential and wherein the polychromatic x-ray source is spaced about four meters from the rotational stage.

24. The scanner of claim 20, wherein the pair of monochromator crystals and wherein the analyzer crystal are selected from the group of non-perfect crystals.

25. The scanner of claim 20, wherein the pair of monochromator crystals are perfect silicon crystals and wherein the analyzer crystal is a perfect silicon crystal.

26. The scanner of claim 20, wherein an existing x-ray source is interchanged with the polychromatic x-ray source which would enable the existing x-ray source to perform phase-contrast imaging.

27. A method of identifying an unknown sample, comprising:

obtaining a known sample;

forming a phase-contrast, x-ray computed tomography image of the known sample;

identifying a diffraction pattern for the known sample using the x-ray computed tomography image of the known sample;

associating the diffraction pattern of the known sample with the known sample in a database;

forming a phase-contrast, x-ray computed tomography image of an unknown sample;

identifying a diffraction pattern for the unknown sample using the x-ray computed tomography image of the unknown sample; and correlating the diffraction pattern of the unknown sample with the diffraction pattern of a known sample using the database;

thereby identifying the unknown sample.

28. The method of claim 27, wherein the known and unknown samples are soft tissue samples.

29. The method of claim 28, wherein the known and unknown samples are biological soft tissue samples.

* * * * *

UNITED STATES PATENT AND TRADEMARK OFFICE
CERTIFICATE OF CORRECTION

PATENT NO. : 7,286,628 B2  
APPLICATION NO. : 10/494635  
DATED : October 23, 2007  
INVENTOR(S) : Edwin F. Donnelly et al.

Page 1 of 1

It is certified that error appears in the above-identified patent and that said Letters Patent is hereby corrected as shown below:

In Title Page, item (60) Related U.S. Application Data, line 1, insert
--Continuation of application No. 10/278,055, filed on October 22, 2002, now abandoned.--

Signed and Sealed this

Fifteenth Day of April, 2008

JON W. DUDAS
*Director of the United States Patent and Trademark Office*